(12) United States Patent
Loughlin

(10) Patent No.: US 7,255,108 B1
(45) Date of Patent: Aug. 14, 2007

(54) APPARATUS FOR INHIBITING OR PREVENTING THE CLENCHING ACTION OF THE JAW

(76) Inventor: Patricia Ann Loughlin, 381 Executive Dr. #402, Carol Stream, IL (US) 60188

( * ) Notice: Subject to any disclaimer, the term of this patent is extended or adjusted under 35 U.S.C. 154(b) by 0 days.

(21) Appl. No.: 10/208,915

(22) Filed: Jul. 31, 2002

Related U.S. Application Data

(60) Provisional application No. 60/309,601, filed on Aug. 3, 2001.

(51) Int. Cl.
*A61F 5/56* (2006.01)

(52) U.S. Cl. .................................. 128/848; 128/857

(58) Field of Classification Search ............... 606/151, 606/157, 158, 204.45, 208; 269/3, 6, 166–171.5; 128/848, 857–862
See application file for complete search history.

(56) References Cited

U.S. PATENT DOCUMENTS

| | | | | |
|---|---|---|---|---|
| 3,575,405 A | * | 4/1971 | Harding | ....................... 269/258 |
| 4,563,921 A | * | 1/1986 | Wallace | ........................ 81/373 |
| 4,926,722 A | * | 5/1990 | Sorensen et al. | .............. 81/487 |
| 5,064,429 A | * | 11/1991 | Waterman et al. | ........... 606/151 |
| 5,464,413 A | * | 11/1995 | Siska et al. | .................. 606/151 |
| 5,551,421 A | * | 9/1996 | Noureldin et al. | ...... 128/207.17 |
| 6,585,243 B1 | * | 7/2003 | Li | ................................. 269/6 |
| 2003/0080485 A1 | * | 5/2003 | Lo | ................................ 269/6 |

* cited by examiner

*Primary Examiner*—Michael A. Brown

(57) ABSTRACT

An apparatus for inhibiting or preventing the clenching action of the human jaw. A lightweight clamping appliance to be worn outside the mouth to inhibit the bite due to the placement of pressure at both sides of the face, beneath the maxilla and above the mandible. A two arm clamp, structurally sized for placement around the outline of the face, with a curved sliding mechanism for altering the length between said arms, and a soft cushioned pad at the end of each clamp arm that can be secured in the desired position. A mechanism for adjusting the applied pressure or tension of the device to individual comfort levels and locking the tension level in place positioned comfortably under the chin area. The elements of the appliance that come into contact with the face during application have cushioned surfaces. An attachable chin cushion provides additional support to the wearer.

4 Claims, 4 Drawing Sheets

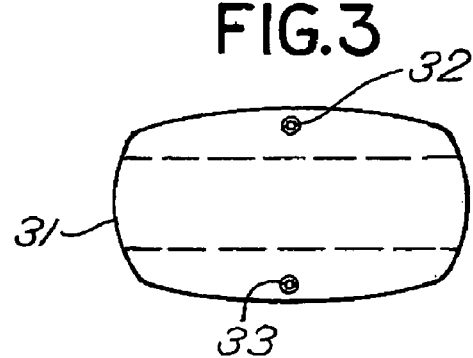
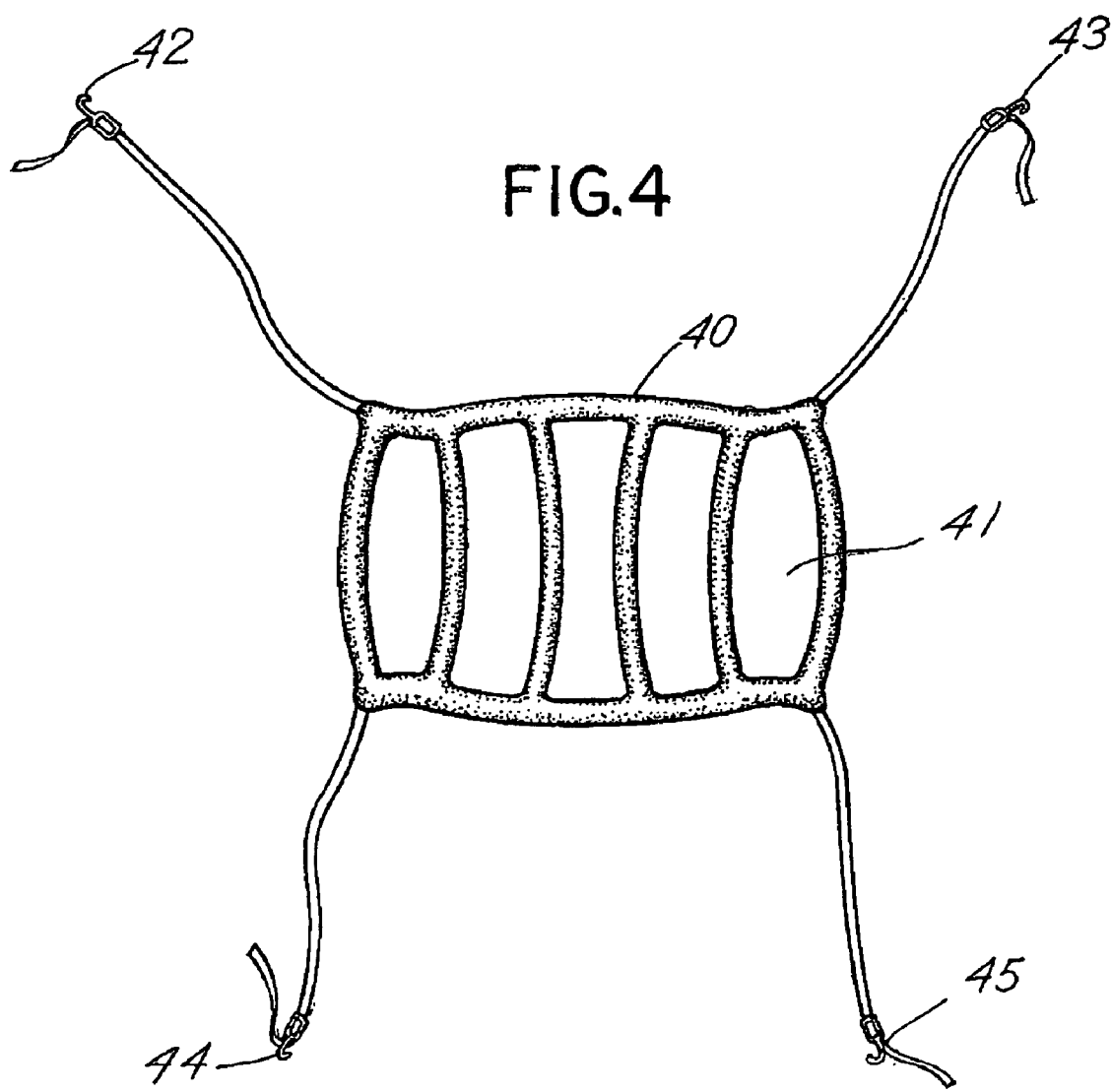

FIG.6
FIG.7
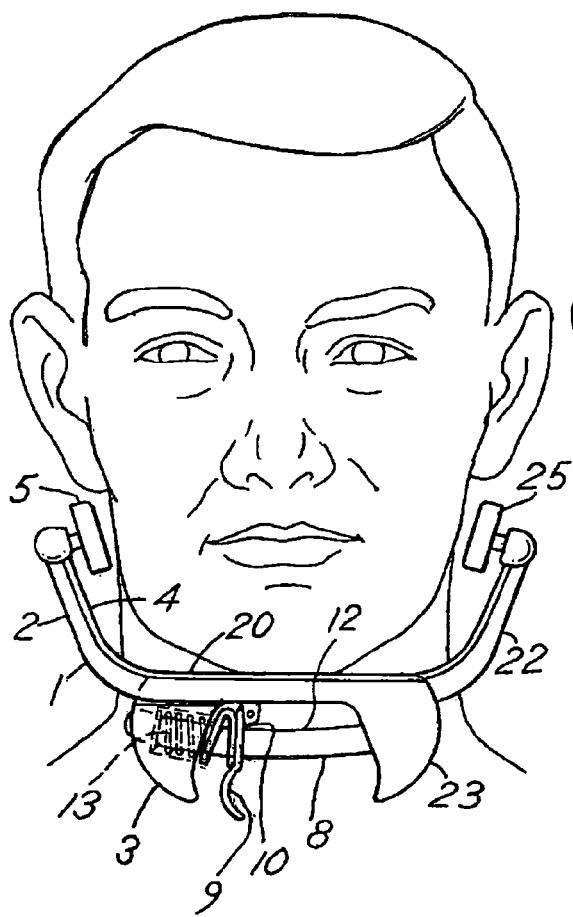
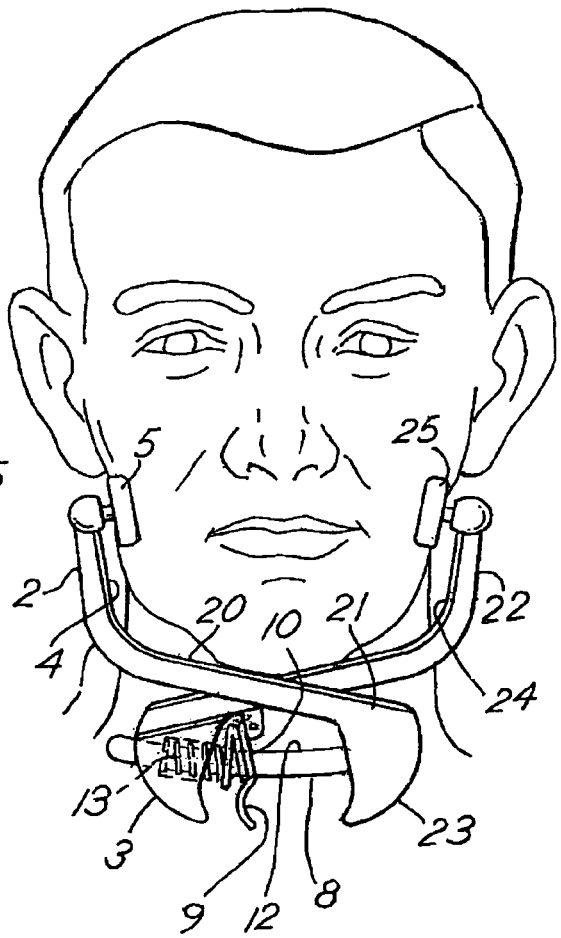

APPARATUS FOR INHIBITING OR PREVENTING THE CLENCHING ACTION OF THE JAW

CROSS REFERENCE TO RELATED APPLICATIONS

This application is based on provisional application Ser. No. 60/309,601, filed on Aug. 3, 2001 (Titled as Jaw Aid).

BACKGROUND OF THE INVENTION

This invention relates generally to the field of oral devices and appliances and more specifically to an apparatus for inhibiting or preventing the clenching action of the jaw. Another way to describe the intention of this apparatus is "to interrupt" the clenching action.

This invention relates to oral devices, appliances and mouthguards used to prevent damage to the soft tissue surrounding the jaw area and the jaw joint itself, and to alleviate or reduce pain in the teeth and jaw muscles created by chronic clenching and/or teeth grinding, primarily while the wearer is sleeping.

Various mouthguard products, both over-the-counter models and doctor-prescribed, are available to sufferers of Temporomandibular Joint Dysfunction (commonly referred to as TMJ or TMJD) and chronic teeth clenchers or grinders. In my experience, however, these products do not address the underlying problem—that the individual's teeth are prone to clench a surface, whether or not it be their own teeth. In the case of an inner mouth appliance, the wearer essentially clenches their teeth against another surface other than their own teeth.

Jaw appliances, that attempt to modify an incorrect bite, or exercise the movements of the jaw, all serve a purpose in trying to identify and correct the individual's chronic maladaptive pattern. However, many of these appliances are prohibitively expensive and time consuming as a pain management approach.

Accordingly, there is a need for a more inexpensive and innovative approach to this problem area of pain management—specifically, for the myofascial tissue in the area surrounding the jaw joint. The model presented herewith possesses certain attributes from the background art for easily-operated hand-clamps, while integrating the characteristics suitable for application to the human jaw joint and surrounding soft tissue area, and overcomes the deficiencies in the currently available products as described above.

Prior art in the area of mouth guards, as found in U.S. Pat. No. 5,823,193 of Singer, describes a mouth guard, or inner mouth appliance, made of soft, rubber-like material that is molded by the individual wearer, without the assistance of a dental professional. Other types of mouth guards widely available are made of hard plastic and are professionally molded by dentists and orthodontic professionals by making an impression of the patient's bite. Great Lakes Orthodontics distributes many products and materials of this type to medical professionals. U.S. Pat. No. 6,241,518 of Sullivan describes an inner mouthguard designed to protect wearers of orthodontic braces from teeth grinding. Other inner mouth guards are covered by U.S. Pat. Nos. 3,496,939 of Gores and 5,082,007 of Adell and were designed for athletes, to protect the player's teeth from biting down abruptly during play. However, these and other inner mouth guards, whether prepared by dentists or orthodontics or self-molded by the wearer, fail to address the biting mechanism— specifically, the chronic overuse of the biting mechanism— and continue to allow for a biting surface (even if a "softer surface" as in the example of U.S. Pat. No. 5,823,193) to come into contact with the teeth. As a result, the teeth are still biting down, often times very hard, on some surface and the jaw muscles are not given time to rest which can lead to problems stemming from overuse. Inner mouth guards, as covered by U.S. Pat. Nos. 3,496,939 of Gores and 5,082,007 of Adell, fall into this category, too, although they are effective for their purpose (worn during activities such as sporting events, to protect the teeth, tongue and jaw from serious injury).

Prior art in the area of jaw appliances as found in U.S. Pat. No. 6,394,799 describe an appliance to correctively position the jaw and features a "pre-set intermediate closure position" and a complete closure position. As described in the preferred embodiments section of the referenced patent, there is "a force that opposes (or resists) the closure movement" and includes attachments (for example, bands) to certain teeth as anchors. The opposition or resistance to the closure movement differs, however, from the invention presented in this patent application in that the biting action is limited, as defined in a "pre-set intermediate closure", but not inhibited or prevented, and the appliance includes intra-oral attachments (for example, bands) to certain teeth as anchors, the management of such would warrant professional dental or oral treatment. The invention described in this application inhibits the biting action, partially by obstructing the pathway of the bite, but also by inhibiting the masseter muscles (of the jaw) from bulking up, which occurs upon contraction. Other jaw appliances, as found in U.S. Pat. No. 6,413,082 of Binder, which provides therapeutic repositioning for a forward displaced jaw, and U.S. Pat. No. 6,413,231 of Berman, which assists individuals with limited jaw opening, are designed for insertion inside the mouth and are professionally administered and managed as well by an oral specialists.

Prior art in the area of hand clamps was found in U.S. Pat. No. 6,367,787 of Poole—a hardware item made by American Tool Companies. Unfortunately, the slide bar of this model extends far out to the side of the appliance, making it impractical for a model-type used as head gear while sleeping. A more recent American Tool Companies product is currently Patent Pending as a curved bar clamp (Quik-Grip Handi-Clamp) which places the trigger mechanism under the body of the clamp (similar to the hand-grip of pliers, but made of hard plastic). But, once again, the device was not intended, nor designed, for application or wear upon the human body, and thus has limiting features in this respect. Since the aforementioned clamps were designed for use on hard structures, such as wood and metal, the essential features of these clamps render them unfeasible for application to any human body part, but particularly to the face due to its delicate anatomy. Aside from the basic structural disadvantages (size, shape and dimension) of prior art for the specific use and application that my invention addresses, they lack the essential comfort feature for wear against the skin of the face that my invention adds. In addition, they were not designed to address the same problem or for the same purpose.

BRIEF SUMMARY OF THE INVENTION

In accordance with the present invention, a lighweight jaw apparatus comprised of two curved arms with soft cushioned pads at each end, a supporting chin cushion and a means for applying tension between said arms. The purpose of the invention is to apply compression to the opposite sides of the face in order to inhibit the biting mechanism and prevent clenching and grinding of the teeth while wearing the apparatus.

OBJECTS AND ADVANTAGES

The primary object of the invention is to provide an innovative approach to relieving overworked and sore muscles that often result from clenching or grinding teeth while sleeping.

Another object of the invention is to provide an alternative to inner mouth appliances, that seek to cushion the bite or maintain an optimal mouth position, by instead inhibiting or preventing the biting mechanism (in other words, "interrupting" the action).

Furthermore, advantages over prior art include:
(a) provides inhibition of the biting mechanism that is in an overuse cycle instead of providing a substitute biting surface,
(b) provides a well-cushioned and padded apparatus, suitable for applying compression to the soft tissues of the face
(c) provides a stabilizing chin cushion and head strap since the clamping apparatus is intended to be worn on the face and movement is inherent Other objects and advantages of the present invention will become apparent from the following descriptions, taken in connection with the accompanying drawings, wherein, by way of illustration and example, an embodiment of the present invention is disclosed.

In accordance with a preferred embodiment of the invention, there is disclosed an apparatus for inhibiting or preventing the clenching action of the human jaw comprising: a clamping appliance to be worn outside the mouth that inhibits the bite due to the placement of pressure at both sides of the face, beneath the maxilla and above the mandible, a 2-arm clamping mechanism, with one arm for placement on each side of the face, a pad at the end of each clamp arm, that could be secured in the desired position against the face, a chin cushion for support and stability during wear, a mechanism for adjusting the applied pressure of the device to individual comfort levels and locking the tension level in place, with the body of said mechanism positioned under the chin area.

BRIEF DESCRIPTION OF THE DRAWINGS

The drawings constitute a part of this specification and include exemplary embodiments to the invention, which may be embodied in various forms. It is to be understood that in some instances various aspects of the invention may be shown exaggerated or enlarged to facilitate an understanding of the invention.

FIG. 3 is an open top view illustrating the chin cushion for the present invention;

FIG. 4 is an open top view illustrating the head support accessory for the present invention;

FIG. 6 is a frontal view illustrating the FIG. 1 clamp, applied without compression (open) to the human jaw;

FIG. 7 is a frontal view illustrating the FIG. 1 clamp, applied with compression (partially closed) to the human jaw.

DETAILED DESCRIPTION OF THE PREFERRED EMBODIMENTS

Detailed descriptions of the preferred embodiment are provided herein. It is to be understood, however, that the present invention may be embodied in various forms. Therefore, specific details disclosed herein are not to be interpreted as limiting, but rather as a basis for the claims and as a representative basis for teaching one skilled in the art to employ the present invention in virtually any appropriately detailed system, structure or manner. In the following drawings, like referenced characters indicate corresponding elements throughout the several views.

Figure 1:
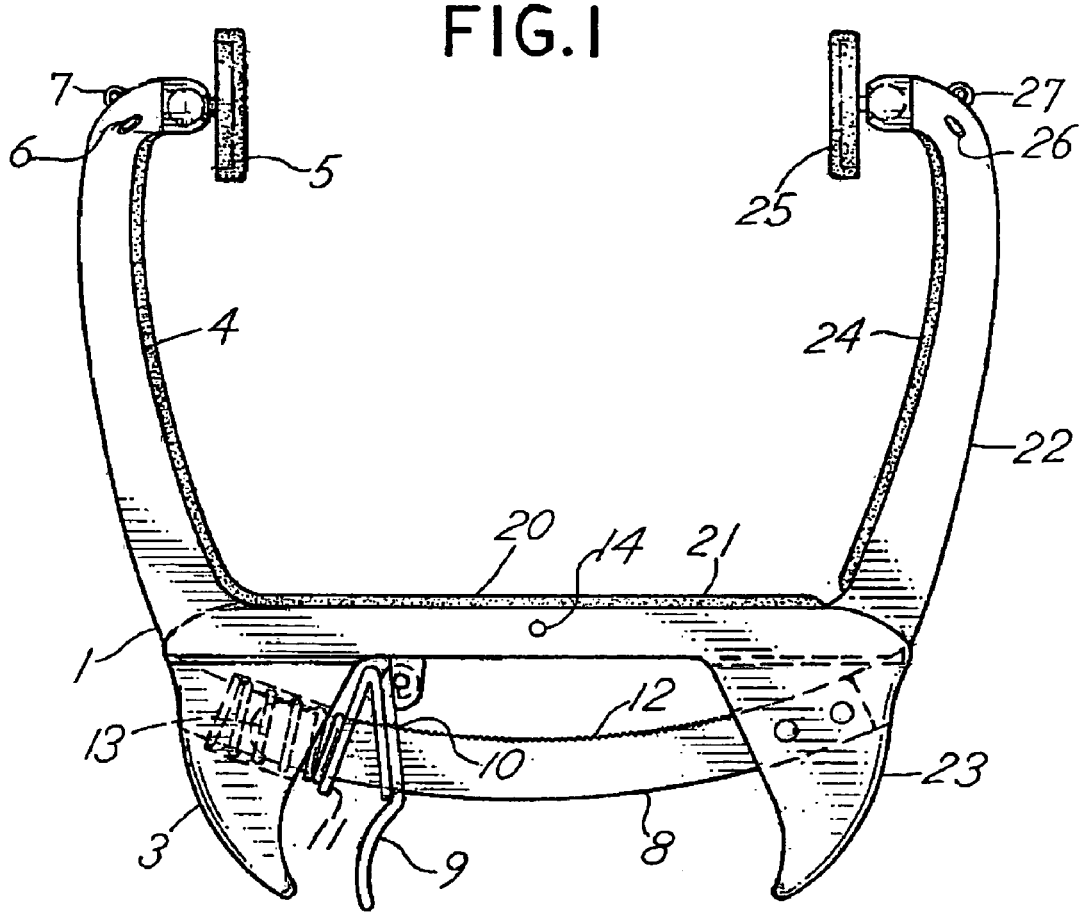
FIG. 1 is a frontal view illustrating a clamp for use on the human jaw of the present invention.

Beginning in FIG. 1, the illustration shows a set of two arms 2 and 22 of lightweight rigid material connected to two sides of the body 1 and 21, which are extensions from the arms connected at the mid-section of the body with a screw 14 inserted through the body side 21 (back) and extending into body side 1 (screw is not shown in this illustration, since FIG. 1 is a frontal view). Finger grip 23 and trigger handle 3 are connected to the body and move in conjunction with the opposite side arm. To illustrate, in FIG. 1, the left arm 2 extends into the front body side 1, which extends into finger grip 23. Alternately, the right arm 22 extends into the backside of the body 21 and further extends into the trigger handle 3. The curved slide bar 8 is underneath the body 1 and 21 and between the finger grip 23 and the trigger handle 3, but moves into the trigger handle upon compression of the handle. The curved slide bar 8 has an upper grooved edge 12 for frictional engagement of the braking lever 10, which is released by the brake release 9. The brake lever pivots against the biasing spring 13, with the assistance of the brake lever support 11. The arms have a cushioned inner surface 4 and 24, as does the upper body 20. The pads 5 and 25 on the end of each arm have cushioned surfaces and are rounded for comfort next to the face. The noncircular chin cushion 31 in FIG. 3 would snap over the body and be secured under the chin. Small outer loops 6, 7, 26 and 27 are available for attachment of the optional head support.

Figure 2:
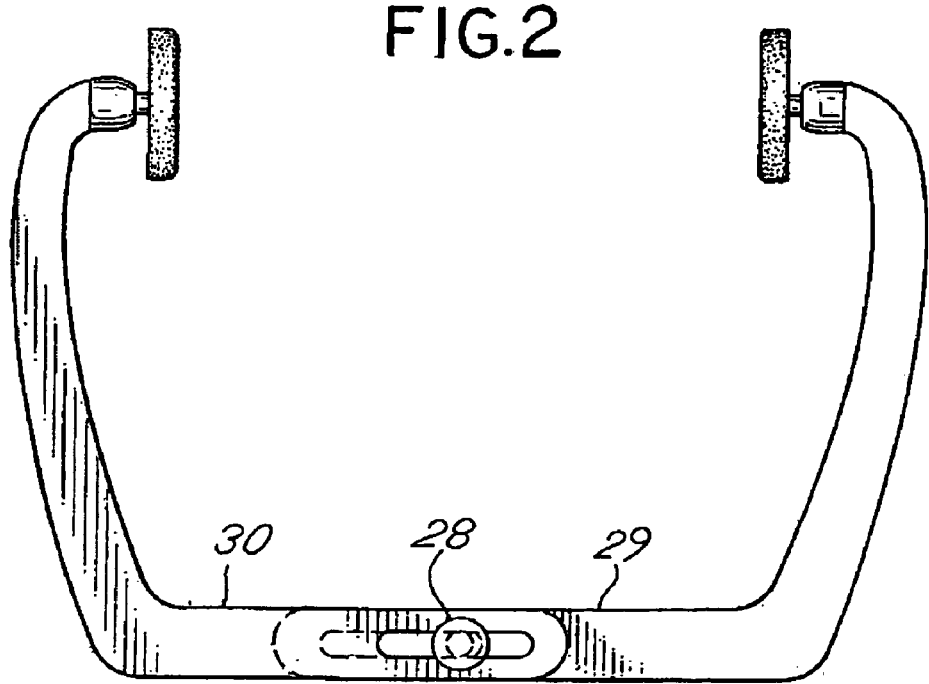
FIG. 2 is a frontal view illustrating a clamp for use on the human jaw of an alternative embodiment of the present invention.

In FIG. 2, an alternative embodiment of the invention is illustrated with the same features as FIG. 1 with the exception of the body slide bar. In this illustration, there is no finger grip or trigger handle. In the case of FIG. 2, the slide bars 29 and 30 move toward each other upon the rotation of a screw 28 in the mid-section of the body. A brake or release mechanism is not a part of this illustration, since it is a simple slide mechanism. The noncircular chin cushion in FIG. 3 would snap 32 and 33 over the body of either embodiment of FIG. 1 or 2.

In FIG. 4, the optional head support is illustrated, indicating a crown 40 with openings 41 for good ventilation around the head and a comfortable fit and attachment points 42, 43, 44 and 45 for connecting to the jaw device at the small outer loops 6, 7, 26 and 27.

Figure 5:
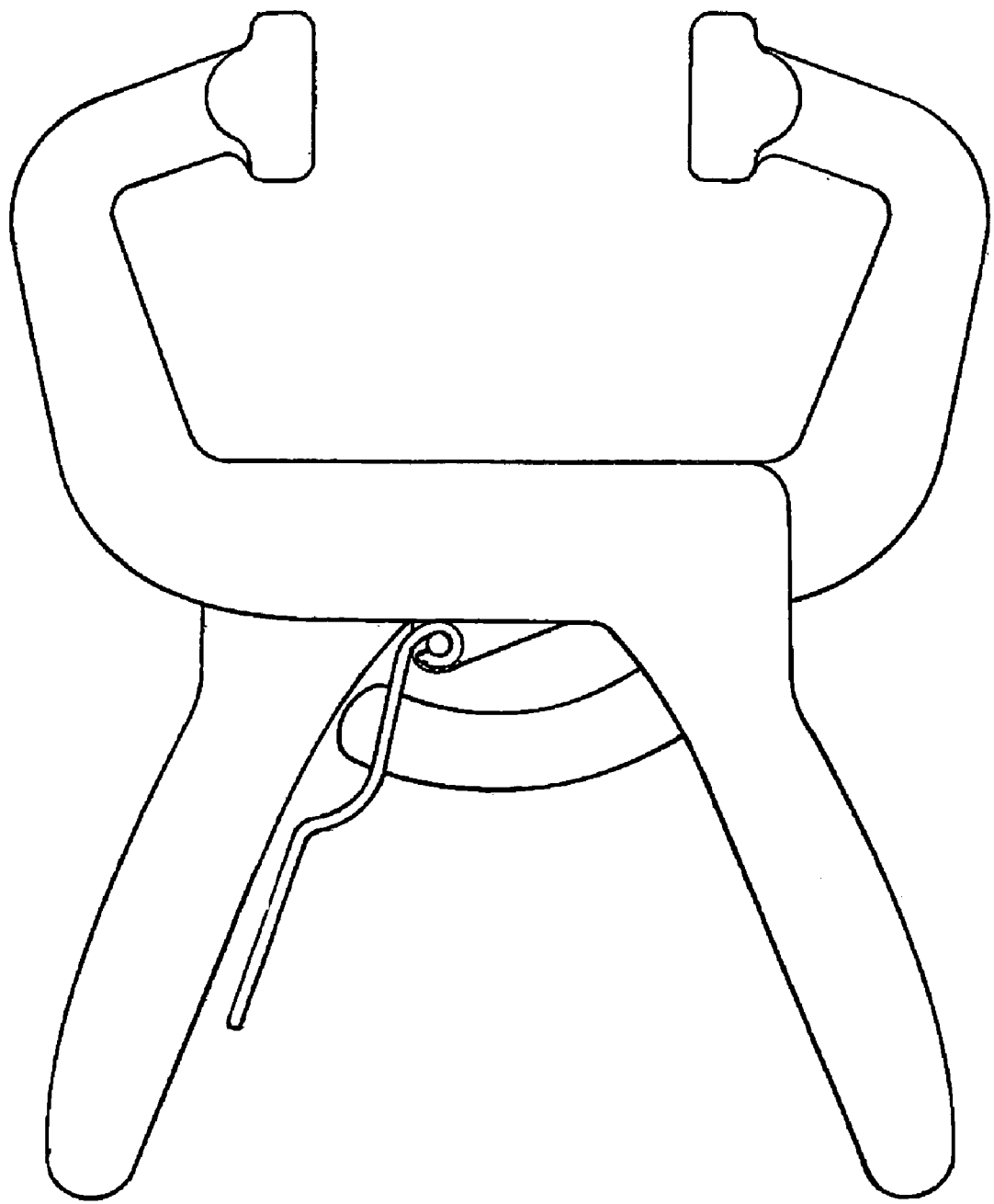
FIG. 5 is a frontal view illustrating an invention disclosed as prior art, made by American Tools Companies, of a curved bar clamp, currently under Patent Pending.

FIG. 5 is an illustration of the American Tools Companies curved bar clamp to indicate the differences between an example of clamp prior art and the invention illustrated in FIG. 1.

FIG. 6 illustrates the invention in FIG. 1 as applied in an open (without compression) position around the jaw. FIG. 7 illustrates a partially closed (with compression) position.

While the invention has been described in connection with a preferred embodiment, it is not intended to limit the scope of the invention to the particular form set forth, but on the contrary, it is intended to cover such alternatives, modifications, and equivalents as may be included within the spirit and scope of the invention as defined by the appended claims.

What is claimed is:

1. An apparatus for inhibiting, preventing or interrupting the clenching action of the human jaw comprising first and second curved arms, adapted to fit on a jaw on each side of the face, said curved arms are formed of lightweight, rigid material, a soft cushioned pad attached to each said curved arm, a curved sliding means for adjusting the length between said curved arms, a chin cushion that is snap fitted onto the apparatus, said chin cushion adapted to support the user's chin, and a biasing spring used to apply tension to said arms of the device.

2. The apparatus as defined in claim 1, wherein said biasing spring is in a position below the chin and produces tension, in synchrony with said curved slide means, upon compression of one arm in the direction of the opposing arm, whereby said slide bar moves inside a cavity in the trigger handle.

3. The apparatus as defined in claim 1, wherein said biasing spring is in a position below the chin and produces tension in synchrony with two opposing slide bars, that move along a horizontal plane toward each other upon compression of the arms, adjustable by means of a lever on the slide bars.

4. The apparatus as defined in claim 1, further comprising a head strap to anchor the appliance in a stable position and to prevent dislodgement of the appliance during wear.

* * * * *